United States Patent [19]

Ward

[11] 4,229,586
[45] Oct. 21, 1980

[54] PROCESS FOR PRODUCTION OF MOTOR FUEL AND PHTHALATE ESTERS OR ACYCLIC ALCOHOLS

[75] Inventor: Dennis J. Ward, South Barrington, Ill.

[73] Assignee: UOP Inc., Des Plaines, Ill.

[21] Appl. No.: 46,282

[22] Filed: Jun. 7, 1979

Related U.S. Application Data

[62] Division of Ser. No. 2,504, Jan. 10, 1979.

[51] Int. Cl.$^2$ .......................... C07C 67/08; C07C 3/16
[52] U.S. Cl. ...................................... 560/98; 585/329
[58] Field of Search ............................ 560/98; 585/329

[56] References Cited

U.S. PATENT DOCUMENTS 2,658,083  11/1953  Burney et al. ...................... 568/882
2,731,503   1/1956  Mattox ................................ 568/882

FOREIGN PATENT DOCUMENTS 619708  5/1961  Canada ...................................... 560/98
809738  3/1959  United Kingdom ...................... 560/98

Primary Examiner—Joseph E. Evans
Attorney, Agent, or Firm—James R. Hoatson, Jr.; John F. Spears, Jr.; William H. Page, II

[57] ABSTRACT

A process for the simultaneous production of gasoline blending components and a phthalate ester useful as a plasticizer. $C_3$ to $C_4$ olefins are reacted in an oligomerization zone to form a mixture containing $C_6$ to $C_{10}$ olefinic hydrocarbons. A three carbon number boiling range intermediate fraction is recovered from this mixture. The less highly branched olefins in this intermediate fraction are selectively hydroformylated to yield alcohols which are then reacted with an aromatic carboxylic acid or an aromatic anhydride. The unhydroformylated olefins are combined with the other olefinic hydrocarbon fractions to form a high octane motor fuel.

6 Claims, 1 Drawing Figure

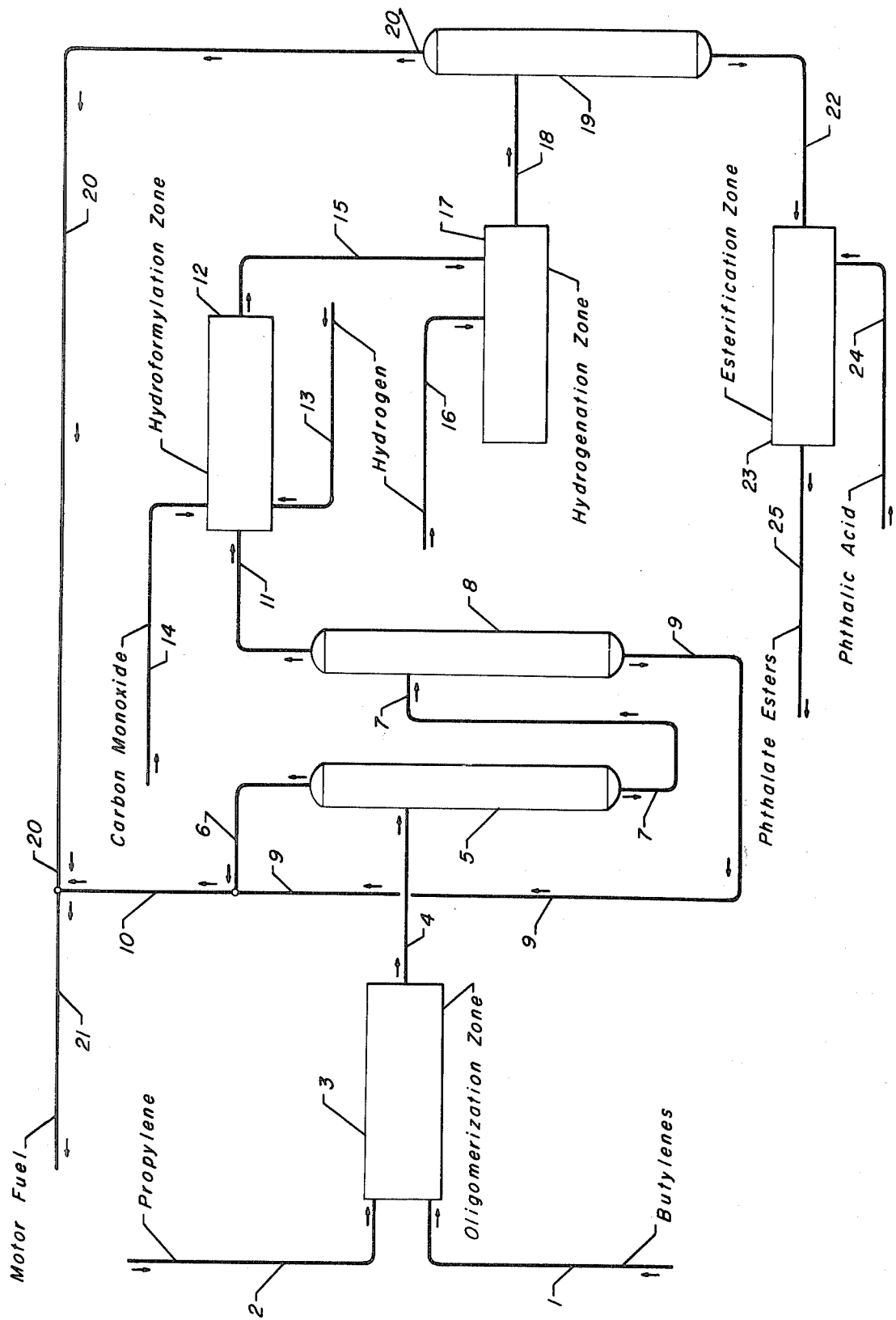

PROCESS FOR PRODUCTION OF MOTOR FUEL AND PHTHALATE ESTERS OR ACYCLIC ALCOHOLS

CROSS-REFERENCE TO RELATED APPLICATION

This application is a Division of prior copending application Ser. No. 2,504 filed on Jan. 10, 1979. The teaching of my prior application is incorporated herein by reference.

FIELD OF THE INVENTION

The invention relates to a hydrocarbon conversion process wherein acyclic alcohols are produced by the hydroformylation of $C_6$-plus olefins. The invention also relates to a process for the production of organic esters by the reaction of an aromatic carboxylic acid or an aromatic anhydride with an acyclic alcohol. The invention further relates to a hydrocarbon conversion process for the simultaneous production of a high octane motor fuel blending component and $C_8$ to $C_{10}$ acyclic alcohols from $C_3$ to $C_4$ olefinic hydrocarbons. The invention specifically relates to a process for producing both a phthalate ester and a high octane gasoline blending stock from $C_3$ and/or $C_4$ olefinic hydrocarbons wherein less highly branched $C_7$ to $C_9$ olefins are preferentially hydroformylated to produce $C_8$ to $C_{10}$ alcohols which are then used in the esterification of an aromatic carboxylic acid or an aromatic anhydride.

PRIOR ART

Both the hydroformylation of olefins and the esterification of carboxylic acids are well documented chemical reactions. The hydroformylation of $C_3$ to $C_{30}$ olefinic hydrocarbons to produce alcohols is described in U.S. Pat. Nos. 3,594,425 and 3,984,478. The esterification of carboxylic acids is a commercial process which is described in Kirk-Othmer *Encyclopedia of Chemical Technology*, 2d Ed., Vol. 8, Interscience Publishers, 1965.

The oligomerization of light olefins is also a well described process and is practiced commercially to produce $C_7$ to $C_{12}$ olefins for use in production of a number of intermediate chemicals and end products including alcohols, detergents and plastics. Oligomerization processes are described in U.S. Pat. Nos. 3,437,708; 3,542,892; 3,906,053; 3,916,019; 3,932,553; 3,959,400; 3,981,941; 3,997,621; 4,000,211; 4,098,839 and 4,113,790. These references present representative catalysts, operating conditions, additives and product yields.

A large amount of phthalate esters are produced for use as plasticizers for polyvinyl chloride polymers and polyvinyl acetate emulsion systems. It is believed that the majority of these esters are presently produced by first fractionating an oligomerization zone effluent, such as a "poly gasoline", into individual narrow boiling range streams comprising heptenes, octenes or nonenes. These streams are then fed either separately or in admixture into hydroformylation zones which are operated at high conversion rates. The material fractionated out between these narrow boiling range cuts is used as gasoline or in some other manner. Therefore, the broad boiling range oligomerization zone effluent stream is subjected to a large number of fractionation steps to separate out individual streams each relatively rich in olefins having the same carbon number. These individual streams are then passed into the hydroformylation zone to produce the plasticizer precursor alcohols. The high or total conversion rates at which the hydroformylation zones are operated results in there being little or no hydrocarbons derived from the hydroformylation zone effluent being available for use as gasoline. The high conversion rates are achieved by the use of selected processing conditions and/or the recycling of unhydroformylated olefins.

BRIEF SUMMARY OF THE INVENTION

The invention provides a synergistic process for simultaneously enhancing the quality of a gasoline blending stream comprising acyclic olefinic hydrocarbons and producing $C_7$ to $C_9$ acyclic alcohols highly suitable for the esterification of cyclic carboxylic acids or anhydrides. This process utilizes a purposely limited conversion in a hydroformylation zone as a substitute for the prior art's extensive fractionation of the acyclic olefinic hydrocarbons fed to the hydroformylation zone. The limited conversion in this zone promotes the preferential hydroformylation of the less branched olefinic hydrocarbons, which yield superior plasticizer precursor alcohols. The remaining selectively unhydroformylated highly branched olefinic hydrocarbons have higher octane numbers than less branched olefinic hydrocarbons and are more desirable gasoline blending components. The invention therefore improves the quality of both the gasoline and the plasticizers which are produced.

One embodiment of the invention may be broadly characterized as a process for the simultaneous production of a phthalate ester and a motor fuel blending stock which comprises the steps of passing a feed stream comprising a $C_3$ olefin into an oligomerization zone and effecting the production of an oligomerization zone effluent stream comprising $C_6$ to $C_{12}$ hydrocarbons including $C_9$ acyclic olefinic hydrocarbons; fractionating the oligomerization zone effluent stream into a light fraction comprising $C_6$ hydrocarbons, an intermediate fraction comprising $C_9$ acyclic olefinic hydrocarbons and a heavy fraction comprising $C_{12}$ hydrocarbons; contacting the intermediate fraction with a hydroformylation catalyst in admixture with carbon monoxide and hydrogen and effecting the production of a hydroformylation zone effluent stream comprising $C_{10}$ acyclic alcohols and at least 20 mole percent $C_9$ acyclic olefinic hydrocarbons; mildly hydrogenating the hydroformylation zone effluent stream; fractionating the hydroformylation zone effluent stream into a light fraction comprising $C_9$ acyclic olefinic hydrocarbons and a heavy fraction comprising $C_{10}$ acyclic alcohols; and contacting the heavy fraction of the hydroformylation zone effluent stream with a monocyclic aromatic polycarboxylic acid or an aromatic anhydride in an esterification zone and effecting the production of an effluent stream comprising the phthalate esters of the $C_{10}$ acyclic alcohols.

DESCRIPTION OF THE DRAWING

The Drawing illustrates the preferred embodiment of the invention. For clarity in describing the inventive concept, various subsystems and assemblies associated with the operation of the process have not been shown. These items include flow and pressure control valves, pumps, temperature and pressure monitoring systems, reactor and fractionator internals, etc., which may be of customary design. This representation of the preferred embodiment is not intended to preclude from the scope of the inventive concept those other embodiments set herein or which are the result of reasonable and normal modification of these embodiments.

Referring now to the Drawing, a feed stream in line 1 comprising butylenes and a feed stream in line 2 comprising propylene is passed into an oligomerization zone 3. This zone is operated at conditions which effect the production of a product stream which is rich in $C_7$ to $C_9$ acyclic olefins. The oligomerization zone effluent stream will also contain other hydrocarbons outside of this carbon number range including $C_6$ and $C_{10}$ olefins. The oligomerization zone effluent stream is passed into a fractionation zone comprising columns 5 and 8 through line 4. A light fraction comprising the relatively lowboiling $C_6$-minus components of the oligomerization zone effluent stream is removed from column 5 as a net overhead stream carried by line 6. The remaining components of the oligomerization zone effluent stream are passed into column 8 through line 7 and separated into an intermediate boiling point range fraction removed in line 11 and a heavy fraction comprising $C_{10}$ olefins removed in line 9 as a net bottoms stream. The light fraction in line 6 and the heavy fraction of line 9 are admixed by passage into line 10.

The thus-separated intermediate $C_7$ to $C_9$ fraction of the oligomerization zone effluent stream is passed into a hydroformylation zone 12 and admixed with hydrogen from line 13 and carbon monoxide from line 14. An intentionally limited conversion of the entering olefins is performed in this zone to produce a hydroformylation zone effluent stream comprising at least 20 mole percent of relatively highly branched $C_7$ to $C_9$ acyclic olefins and a higher concentration of less highly branched $C_8$ to $C_{10}$ acyclic aldehydes and alcohols. This effluent stream is passed through line 15 into a hydrogenation zone 17. Hydrogen from line 16 is utilized to effect the selective catalytic hydrogenation of the aldehydes to alcohols and to thereby produce a hydrogenation zone effluent stream comprising $C_7$ to $C_9$ acyclic olefins and $C_8$ to $C_{10}$ acyclic alcohols.

The hydrogenation zone effluent stream is passed into a fractionation column 19 through line 18. The $C_7$ to $C_9$ olefins in this effluent stream are concentrated into a net overhead stream carried by line 20 to the junction with line 10. The streams in these two lines are then combined to form a high octane motor fuel blending stock removed as a product stream in line 21. The $C_8$ to $C_{10}$ alcohols contained in the hydrogenation zone effluent stream are concentrated into a net bottoms stream carried by line 22 and passed into an esterification zone 23. A stream of phthalic acid in line 24 is also passed into the esterification zone, with the acid being reacted with the alcohols to form phthalate esters which are removed as a product stream in line 25.

DETAILED DESCRIPTION

Large amounts of aromatic esters are produced annually by the esterification of cyclic carboxylic acids. These acids are normally polydicarboxylic acids, with the dicarboxylic acids predominating. An example is the esterification of phthalic acid (o-benzene dicarboxylic acid) with one or more acyclic alcohols having from about 7 to about 11 carbon atoms per molecule to produce phthalate esters which are widely used as plasticizers. These plasticizers are useful for compounding into polyvinyl chloride and other polymers. Many aromatic esters also have utility as herbicides. Aromatic esters may also be produced by the esterification of an aromatic anhydride, such as phthalic anhydride, with the acyclic alcohol.

Acyclic long chain alcohols are also often referred to as oxo alcohols since many are produced in an "oxo" or hydroformylation unit. They are widely used in a great number of applications in addition to ester production. These include use as plasticizers, lacquer solvents, antifoam agents, or in perfumes and industrial odorants. The feed material to the oxo process unit consists of one or more olefinic hydrocarbons having one less carbon atom per molecule than the desired alcohol(s). One method of producing these olefinic hydrocarbons, which may have from about 6 to about 10 carbon atoms per molecule, is by the oligomerization of $C_3$ and/or $C_4$ olefins. These lighter olefins are in abundant supply as the byproducts of fluidized catalytic cracking (FCC) operations present in most petroleum refineries, and they may be produced by thermocracking heavier hydrocarbons.

The oligomerization processes available today produce a product stream containing a wide range of different olefinic compounds. That is, an oligomerization process designed and operated to produce $C_9$ olefins from propylene will also produce $C_6$ and $C_{12}$ olefins. When the feed stream contains both propylene and mixed butylenes, the product stream may contain hydrocarbons having every carbon number from 6 to 12 or higher. If it is desired to utilize only the $C_7$ and $C_9$ olefins or only the $C_6$ and $C_8$ olefins produced in this manner as the feed to the hydroformylation zone, it is necessary to perform four fractionation steps. For instance, to recover the $C_7$ and $C_9$ olefins, it is necessary to first remove the "light polymer" compounds having boiling points below that of the heptenes. In the second fractionation step, the heptenes are recovered as an overhead product. The bottoms material which remains after the heptenes are recovered is fractionated off in a third column to remove all compounds having boiling points below nonene. The bottoms stream of the third column is then passed into a fourth column, from which the nonenes are removed overhead while the remaining "heavy polymer" is removed as a bottoms product. The three undesired olefin fractions are then combined and may be used as a gasoline blending stock. The oligomerization zone is sometimes operated for the specific purpose of making "poly gasoline" from light olefins, with this fractionation procedure being performed to extract the desired olefins from this gasoline.

These complex fractionation procedures require a large capital expenditure for a multiplicity of fractionation columns and also consume a sizable amount of energy. The fractionation requirements are further complicated by the fact that some of the specific isomers contained in a one carbon number fraction, such as the heptene fraction, are undesirable as charge stocks for the oxo operation and require careful fractionation to be excluded, to the extent practical, from the net heptene product. Despite these problems, this costly fractionation sequence is still being employed to obtain olefins which are to be converted into alcohols.

The long chain olefins recovered in the fractionation procedure are then passed into a hydroformylation zone. It is believed the customary practice in the production of plasticizer precursor alcohols is to operate this zone in a manner which consumes essentially all of the olefinic hydrocarbons in the feed stream. This high rate of conversion may be achieved by a combination of selected processing conditions and the recycling of unconverted olefinic hydrocarbons.

It is an objective of the subject invention to provide a process for the simultaneous production of an acyclic alcohol having at least 7 carbon atoms per molecule and a high octane motor fuel blending stock.

It is another objective of the subject invention to provide a process for the production of an aromatic ester.

It is a further objective of the subject invention to provide a process for the simultaneous production of a high octane motor fuel blending stock and an aromatic ester.

These objectives are achieved in the subject process in a series of steps which includes passing the long chain $C_6$-plus olefinic hydrocarbons into a hydroformylation zone intentionally operated at a relatively low total conversion rate. Specifically, the hydroformylation zone is operated in a manner which effects from about 30 to about 80 mole percent conversion of the olefinic hydrocarbons. The hydroformylation zone preferably operates on a "once-through" basis without any recycling of unconverted olefinic hydrocarbons.

The specification of a preferred conversion range is actually only a quantitative expression of the desired conversion criteria. The real goal is the selective hydroformylation of the less highly branched olefins. At the same time, it is desired that the majority of the relatively highly branched olefins are not converted to aldehydes or alcohols within the hydroformylation zone. The very great number of possible compounds in the hydroformylation zone feed stream and effluent stream and the difficulty of analyzing for each of them makes it extremely difficult to characterize this aspect of the inventive concept in a more precise manner. However as a general rule, the reactivity or ease of conversion of the olefins decreases as the olefin becomes more highly branched, with n-olefins being the most easily converted. As used herein, the phrase "conditions under which the majority of the relatively high octane number acyclic olefins are not converted" and equivalent phrases are intended to indicate conditions at which less than 60 mole percent of any dialkyl olefins in the feed stream are reacted and at which less than 90 mole percent of any trialkyl olefins are consumed in the reaction. At the same time, the preferred reaction conditions should result in the ultimate conversion of at least 80 mole percent of any normal olefins to alcohols. Desired overall olefin conversions are set out below.

The subject process provides a definite synergistic effect. By selectively consuming the less highly branched olefins, it performs a separation by octane number thereby leaving the higher octane olefins for use as gasoline. The octane number of the product gasoline is thereby improved by blending the unconverted olefinic hydrocarbons back into the remaining components of the oligomerization zone effluent stream. At the same time, the less highly branched alcohols produced in the subject process normally produce better quality plasticizers when used to form aromatic esters. That is, the subject invention improves the quality of two different products, the aromatic ester plasticizers and the motor fuel blending stock. In addition, the subject process is believed to offer significant savings in both utilities and capital costs compared to the prior art processes which require extensive fractionation of the oligomerization zone effluent.

One embodiment of the subject invention may be characterized as a process for the production of an aromatic ester and a gasoline blending stock which comprises the steps of passing a feed stream comprising a $C_3$ and a $C_4$ olefin into an oligomerization zone operated at oligomerization-promoting conditions and effecting the production of an oligomerization zone effluent stream comprising $C_6$ to $C_{10}$ hydrocarbons including $C_7$ to $C_9$ acyclic olefinic hydrocarbons; fractionating the oligomerization zone effluent stream into a light fraction comprising $C_6$ hydrocarbons, an intermediate fraction comprising $C_7$ to $C_9$ acyclic olefinic hydrocarbons and a heavy fraction comprising $C_{10}$ hydrocarbons; contacting the intermediate fraction with a hydroformylation catalyst at hydroformylation conditions in admixture with carbon monoxide and hydrogen and effecting the production of a hydroformylation zone effluent stream comprising $C_8$ to $C_{10}$ acyclic aldehydes, $C_8$ to $C_{10}$ acyclic alcohols and at least 20 mole percent $C_7$ to $C_9$ acyclic olefinic hydrocarbons; passing the hydroformylation zone effluent stream through a hydrogenation zone operated at aldehyde hydrogenation conditions and effecting the formation of a hydrogenation zone effluent stream; fractionating the hydrogenation zone effluent stream into a light fraction comprising $C_7$ to $C_9$ acyclic olefinic hydrocarbons and a heavy fraction comprising $C_8$ to $C_{10}$ acyclic alcohols; contacting the heavy fraction of the hydrogenation zone effluent stream with a monocyclic aromatic carboxylic acid or an aromatic anhydride in an esterification zone maintained at esterification-promoting conditions and effecting the production of an esterification zone effluent stream comprisig an aromatic ester; recovering the aromatic ester from the esterification zone effluent stream; and producing a product stream suitable for use as a high octane blending stock by admixing the light and heavy fractions of the oligomerization zone effluent stream and the light fraction of the hydrogenation zone effluent stream.

A feed stream comprising one or more light olefins is passed into the oligomerization zone. As used herein, the term "light olefin" is intended to indicate an olefin which exists as a vapor at a temperature of 25° C. and a total imposed pressure of 1 atmosphere absolute. The feed stream may therefore contain ethylene, propylene, butene-1 and butene-2. The feed stream will preferably contain a mixture of propylene and one or more butenes. $C_5$ olefins may also be charged to the oligomerization zone if desired. The feed stream may also contain saturated hydrocarbons having similar boiling points such as propane and butane. Suitable light olefins for charging to the oligomerization zone may be obtained from a fluidized catalytic cracking (FCC) process unit which is utilized in most modern petroleum refineries.

The oligomerization zone may take several forms depending on such variables as the catalyst which is employed within this zone. For instance, U.S. Pat. Nos. 3,932,553 and 3,997,621 describe processes in which boron trifluoride is utilized as a catalyst. Both of these catalytic systems utilize a minor amount of an additive to control the extent to which the oligomerization proceeds. In both of these references, the catalyst system appears to be homogeneous. Heterogeneous catalytic systems for the production of higher molecular weight olefins by the oligomerization or dimerization of light olefins are described in U.S. Pat. Nos. 3,906,053; 3,916,019; 3,959,400; 3,981,940 and 3,981,941. As may be expected from the large number of available oligomerization processes, the conditions employed within the oligomerization zone may vary widely. For instance, the just cited references specify that the reaction may be performed at temperatures ranging from −50° C. to 250° C. and at a pressure ranging from about 1.3 atmospheres gauge to approximately 100 atmospheres gauge.

The preferred catalyst for use in the oligomerization zone is an SPA (solid phosphoric acid) type catalyst. As used herein, the term "SPA catalyst" is intended to indicate a solid catalyst which contains as one of its principal ingredients an acid of phosphorus such as an ortho-, pyro- or tetra-phosphoric acid. The catalyst is normally formed by mixing the acid of phosphorus with a siliceous, solid carrier to form a wet paste. This paste may be calcined and then crushed to yield catalyst particles, or the paste may be extruded or pelleted prior to calcining to produce more uniform catalyst particles. The carrier is preferably a naturally occurring porous silica-containing material such as kieselguhr, kaolin, infusorial earth and diatomaceous earth. A minor amount of various additives, such as mineral talc, fullers earth and iron compounds including iron oxide may be added to the carrier to increase its strength and hardness. The combination of the carrier and the additives preferably comprises about 15–30% of the catalyst, with the remainder being the phosphoric acid. The additive may comprise about 3–20% of the total carrier material. Variations from this such as a lower phosphoric acid content are however possible. Further details as to the composition and production of SPA catalysts may be obtained from U.S. Pat. Nos. 3,050,472; 3,050,473 and 3,132,109 and from other references.

The catalyst is preferably disposed in fixed beds within the oligomerization zone. Either a tubular or chamber-type reactor structure may be used. In a tubular reactor, the catalyst is placed in relatively small diameter tubes which are surrounded by a water jacket to remove the heat liberated by the exothermic reaction. Steam generated in this manner can be used to preheat the feed. In a chamber-type reactor, the reactants flow through a series of large diameter catalyst beds. The temperature of the reactants is controlled by recycling relatively inert hydrocarbons which act as a heat sink or by the use of a quench between vertically stacked catalyst beds. The quench material is the same as that used as the recycle stream, and both methods of temperature control may be used simultaneously. The different catalyst beds are preferably contained within a single, cylindrical, vertically oriented vessel, and the feed stream preferably enters the top of the polymerization zone. A chamber-type reactor containing about five catalyst beds is preferred.

The oligomerization zone is maintained at oligomerization-promoting conditions. These conditions may vary widely due to the previously listed variables. A broad range of suitable pressures is from about 15 psig. to about 1200 psig., with a preferred pressure range for an SPA catalyst being from 400 to 1000 psig. The temperature maintained in this zone with the preferred SPA catalyst may vary from about 120° C. to about 260° C. Steam or water may be fed into the polymerization zone to maintain the desired water content in the preferred catalyst.

In the preferred embodiment, an SPA catalyst is utilized in a chamber-type oligomerization zone to form a net effluent having a gasoline boiling point range of about 43° C. to about 215° C. as determined by the appropriate ASTM distillation method. The feed stream is first commingled with a recycle stream comprising propane and butane which is used as a temperature controlling diluent. It is then heat exchanged with the oligomerization zone effluent, further heated and passed into the top of the oligomerization reactor. Additional amounts of a propane/butane-rich coolant similar in composition to the recycle stream are added between each of the catalyst beds.

The effluent of the oligomerization reactor is preferably heat exchanged against the feed stream to this zone and then flashed. The resulting flash drum vapor stream is cooled to form a liquid stream used as part of the recycle stream. The flash drum liquid stream is passed into an intermediate point of a fractionation column utilized as a stabilizer. The overhead vapors of this column are condensed to form reflux and a net overhead liquid stream. This overhead liquid stream is combined with the liquid stream of flash drum condensate to form the total recycle stream. Low boiling oligomers may be returned to the oligomerization zone in this manner to effect their further oligomerization. The gasoline boiling range oligomerization product is recovered as the bottoms stream of the fractionation column. Oligomerization zones using other than the preferred catalyst may differ substantially in their arrangement and operation from this preferred oligomerization zone configuration.

The net effluent of the oligomerization zone is passed into a first separation zone which preferably is a fractionation zone. This first fractionation zone may comprise two multi-tray fractionation columns arranged in the manner shown in the Drawing. The design and operation of these columns is determined largely by the composition of the oligomerization zone effluent stream and the desired carbon number range of the olefins which are charged to the hydroformylation zone. The columns are preferably operated at a superatmospheric pressure less than about 35 atmospheres absolute and with a bottoms temperature in the broad range of about 120° C. to about 325° C. The hydroformylation zone feed stream produced in this fractionation zone consists of an intermediate fraction or boiling point range portion of the total oligomerization zone effluent stream. This intermediate fraction will contain an exceptionally diverse mixture of olefinic hydrocarbons varying in structure from n-olefins to highly branched olefins. All of the olefins may have the same carbon number (carbon atoms per molecule) or they may have a carbon number range of two or three. The intermediate fraction preferably comprises olefinic hydrocarbons having from 7 to 9 carbon atoms per molecule.

The olefin-containing intermediate fraction of the oligomerization zone effluent stream is charged into a hydroformylation zone in admixture with carbon monoxide and hydrogen, which are also reactants in the oxo process. In the hydroformylation reaction, a carbon atom and an oxygen atom are added to an olefin. This results in the production of a mixture of aldehydes and alcohols having a carbon number one greater than the olefinic hydrocarbons consumed in the reaction. The aldehydes are subsequently hydrogenated to yield additional alcohols.

Either a homogeneous or a heterogeneous catalyst system may be employed in the hydroformylation zone. The reactor configuration will be largely determined by the type of catalyst used and the choice between continuous and batch operation of the hydroformylation zone. Preferably, one or more fixed bed reactors or reaction stages are employed. The hydrocarbon reactants are preferably not recycled. That is, the hydroformylation zone is preferably operated as a continuous "once-through" process step. Gaseous portions of the reactor effluent may be recycled to conserve hydrogen and carbon monoxide. The preferred catalyst is a metal phthalocyanine compound dispersed on an inert support. The metal may be selected from the group consisting of rhenium, rhodium, cobalt, ruthenium, iridium and osmium. The inert support may be gamma-alumina, silica, silica-alumina mixtures, mordenite, fautasite, etc., with gamma-alumina being preferred. Further details on the preferred catalyst system may be obtained by reference to U.S. Pat. No. 3,984,478. Other catalyst systems for hydroformylation are described in U.S. Pat. Nos. 3,594,425 and 4,108,905.

The hydroformylation zone is operated at hydroformylation conditions under which the majority of the relatively high octane number acyclic olefins are not reacted. The desired degree of conversion of specific classes of the olefins has been set out in quantitative terms above. Less than about 80 but more than about 30 mole percent of the total olefinic hydrocarbons present in the hydroformylation zone feed stream are to be reacted to produce oxygen-containing compounds. That is, the net hydrocarbonaceous effluent of the hydroformylation zone contains at least 20 mole percent acyclic olefinic hydrocarbons and may contain up to about 70 mole percent olefinic hydrocarbons. Preferably, there is less than 70 mole percent conversion of the acyclic olefinic hydrocarbons to alcohols in the hydroformylation zone. Operation of the hydroformylation zone at these relatively mild conditions effects a fairly selective oxidation of the normal or straight chain olefins, which have the lowest octane number of those olefins having the same carbon number. As a general rule, the rate of reaction of the olefins in the hydroformylation zone decreases as the structure of the olefin becomes more highly branched. The unreacted remaining olefinic hydrocarbons therefore form a mixture which is rich in the more highly branched high octane olefins. The hydroformylation zone may be operated at a temperature of from about 15° to about 300° C. with a pressure of from about 1 to 300 or more atmospheres gauge. The preferred operating temperature is in the range of 70° C. to 180° C.

The effluent stream of the hydroformylation zone comprises a mixture of the alcohols and aldehydes produced in this zone and the unconverted olefins. This stream is passed into a hydrogenation zone operated at conditions which effect the selective hydrogenation of substantially all of the aldehydes to additional alcohols. This hydrogenation may be integrated with the hydroformylation zone and is often considered to be part of the hydroformylation zone. Rather mild aldehyde hydrogenation conditions are sufficient for this zone since it is not desired to hydrogenate either the alcohols or olefins present in the hydroformylation zone effluent stream. The temperature may range from about 100° C. to about 230° C. and the pressure is preferably below 150 atmospheres but above 20 atmospheres of hydrogen. A solid copper chromite catalyst such as "G13" or "G22" supplied by United Catalyst Inc. of Louisville, Kentucky may be employed.

The effluent stream of the hydrogenation zone is passed into a second fractionation zone. Preferably, this second fractionation zone comprises a single multitray fractionation column. The hydrogenation zone effluent stream is therein separated into a relatively lowboiling or light fraction and heavy fraction. The light fraction contains essentially all of the olefinic hydrocarbons originally present in the hydrogenation zone effluent stream and is therefore rich in these hydrocarbons. The heavy fraction contains essentially all of the acyclic alcohols originally in the hydrogenation zone effluent stream. The light fraction is removed as a net overhead stream and is combined with the portion(s) of the oligomerization zone effluent stream which are separated out during the preparation of the hydroformylation zone feed stream in the first fractionation zone. The light fraction may therefore be admixed with a single fraction or both the heavy and light fractions as in the preferred embodiment. The result of this admixture is a motor fuel blending stock having a higher octane number than the oligomerization zone effluent stream and preferably having a boiling point range within that of good quality gasoline.

After any further fractionation which may be required to remove heavy tars formed in the hydroformylation zone, the alcohol-containing heavy fraction of the hydroformylation zone effluent stream is passed into an esterification zone and therein reacted with an aromatic carboxylic acid or an aromatic anhydride. The aromatic carboxylic acid may be any one of the many compounds in this category including benzoic, phthalic, isophthalic, terephthalic, hemimellitic, trimellitic and benzene pentacarboxylic acids. Preferably, the acid is a benzene dicarboxylic acid, with phthalic acid being especially preferred. The anhydride reacted in the esterification zone is preferably phthalic anhydride, but other anhydrides can be employed if desired.

The alcohol-containing fraction charged to the esterification zone is a mixture of a very large number of different alcohols. These alcohols will vary in both their carbon number and in their molecular structure. There are probably at least 100 different alcohols present in a $C_8$ to $C_{10}$ alcohol fraction, with this fraction possibly containing 200 or more different alcohols. When a dicarboxylic acid is charged to the esterification zone, any two of these alcohols may react with it. The product stream of the esterification zone may therefore contain literally hundreds of different esters. Among the esters which may be present in this stream are such widely used compounds as diisodecyl phthalate and diisooctyl phthalate and mixed esters including amyl decyl phthalate and butyl benzyl phthalate.

The esterification zone may be operated in a continuous or batch mode. The catalyst employed is normally a strong mineral acid such as sulfuric acid and phosphoric acid. Boron trifluoride, benzenesulfonic acid and p-toluenesulfonic acid are also catalysts for the esterification of aromatic acids. Solid cation exchange resins which contain strongly acid groups such as regenerable phenol-formaldehyde resins containing sulfonic acid groups may also be used as the catalyst. A hydrocarbon entrainer for the coproduced water is usually added to the reaction mixture. Toluene is a suitable water entrainer.

An excess of the alcohol is desirable in the esterification zone, but the total amount of alcohol charged is preferably less than twice the amount consumed in the reaction. The esterification zone may be operated at a temperature of from about 20° C. to about 125° C. or higher. The water released in the esterification reaction may be removed by distillation to drive the reaction to higher degrees of completion. The esterification should be maintained at a pressure sufficient to maintain the aromatic acid or anhydride and substantially all of the alcohol in a liquid phase. A pressure in the range of 1.0 to about 75 atmospheres absolute is preferred.

EXAMPLES

The benefits derivable from the subject invention are demonstrated by the following examples. The feed stream used in experiments was a mixture of $C_7$ to $C_9$ olefinic hydrocarbons produced by the SPA catalyzed oligomerization of $C_3$ and $C_4$ olefins. The carbon number distribution of the feed stream was approximately 26% $C_7$, 54% $C_8$ and 20% $C_9$. The feed stream was passed through a bed of silica gel to reduce peroxides to a concentration below 0.1%.

All four experiments were performed in the same manner, with hydroformylation temperature being the only intentional and significant variable between the experiments. In each run, 500 ml of the olefin feed mixture were passed through 50 gm of 60-200 mesh silica gel and then charged to a 1.0 liter stirred autoclave in admixture with a chlororhodium phthalocyanine tetrasulfonate catalyst. The autoclave was flushed with nitrogen and then pressurized with a 2:1 mixture of hydrogen and carbon monoxide. The autoclave was then heated to the desired reaction temperature. A continuous feed of a mixture of hydrogen and carbon monoxide was then passed into the autoclave at a pressure of 2500 psig.

After six hours, the reaction mixture was cooled to room temperature. The organic material was removed from the autoclave and washed with a saturated $NaHCO_3$ solution and deionized water. It was then dried and filtered. The resultant hydroformylation product was then hydrogenated to convert aldehydes to the desired alcohols. The hydrogenation was performed in a 1.0 liter stirred autoclave using a copper chromite ($CuCr_2O_4$) catalyst. The autoclave was maintained at a temperature of about 175° C. for 12 hours after being pressurized with 100 atmospheres of hydrogen. The product of this reaction was contacted with potassium hydroxide to saponify any formate ester, drained of an aqueous layer, neutralized, washed and vacuum filtered. The hydrogenation product was then fractionated to yield olefinic and alcohol fractions.

The alcohol fraction was esterified following a published method (Hatch, Higher Oxo Alcohols, pages 39-42). The alcohol fraction and phthalic anhydride were added in a 2.3:1.1 molar ratio to a one liter stirred flask equipped with a Dean-Stark condenser. Following the reference, the catalyst (p-toluenesulfonic acid) was added based on the percent excess alcohol present. Toluene was used as the solvent. The reaction mixture was brought to reflux until the theoretical amount of water was collected. The resultant mixture was washed with an NaOH solution and deionized water, dried, vacuum filtered and vacuum stripped of remaining toluene. After vacuum distilling off any unreacted alcohol, the product was decolorized with activated carbon to yield the desired plasticizers.

The tables below are useful in comparing the data obtained following this procedure. The two missing percentages in Table 2 have been deleted since the original data appears inaccurate due to analytical problems. To facilitate analysis, the hydrocarbon fraction was hydrogenated. The results in Table 2 therefore are listed by the paraffins produced in the hydrogenation. All percentages are weight percentages.

TABLE 1

| Test No. | Hydroformylation Temperature (°C.) | % Olefin Conversion | Octane No. |
|---|---|---|---|
| 1 | 90 | 37 | 97.8 |
| 2 | 100 | 47 | 97.9 |
| 3 | 110 | 70 | 95.7 |
| 4 | 125 | 93 | 88.8 |

TABLE 2

(Olefinic Fraction Comparison)

| Test No. | 1 | 2 | 3 | 4 |
|---|---|---|---|---|
| | % Conversion | | | |
| 2,3-dimethylpentane | 44.7 | 60.7 | 74.9 | 96.1 |
| 2,4-dimethylhexane | 33.5 | 45.1 | 76.1 | 97.1 |
| 2,3,4-trimethylpentane | 27.5 | 33.5 | 54.4 | 89.4 |
| 2,3-dimethylhexane and 2-methyl-3-ethyl pentane | 32.9 | 40.7 | 64.5 | 94.4 |
| 3,4-dimethylhexane and 3-methyl-3-ethyl pentane and 2,2,4,4-tetramethylpentane | 29.1 | 41.3 | 69.5 | 95.9 |
| 2,2,5-trimethylhexane | 8.1 | 16.1 | 52.5 | — |
| 2,3,5-trimethylhexane | 4.6 | — | 30.6 | 78.0 |
| 2,3,4-trimethylhexane and 2,2,3,3-tetramethylpentane | 0.0 | 0.0 | 30.0 | 74.9 |

The data in Table 1 indicates that as the temperature of the hydroformylation is increased, the percentage conversion increases and the research clear octane number of the unconverted olefinic hydrocarbons decreases. The octane number of the SPA olefins prior to hydroformylation was approximately 95.

The data in Table 2 also shows the conversion of the olefinic hydrocarbons increased as the temperature is increased. In addition, it indicates that at lower conversion rates, the more highly branched olefinic hydrocarbons are consumed to a lesser extent in the hydroformylation reaction. The concentration of the desired less highly branched alcohols in the effluent of the hydroformylation zone will therefore be significantly greater at lower conversion rates than the concentration of less highly branched olefins in the feed stream to the hydroformylation zone. The plasticizers produced from these alcohols should therefore be of better quality than those produced at high conversion rates. At the same time, the octane number of the gasoline blending stream formed from the feed olefins may be improved by the addition of high octane components which are not consumed at the relatively low hydroformylation conversions. The synergistic effect of the process in improving two totally different products is therefore apparent in the experimental results.

In another embodiment of the invention, the conditions employed within the hydrogenation zone are more severe, with the result that a sizable percentage or all of the olefins present in the hydroformylation zone effluent are saturated within this zone. This embodiment is not preferred as it may result in the production of a lower octane number motor fuel blending stock. In this embodiment of the invention, the stream charged to the second separation zone will be a mixture comprising paraffins and alcohols, with the paraffins being concentrated into the light fraction and the alcohols being concentrated into the second high boiling fraction. In all other respects, this embodiment of the invention would be performed in the same manner as those previously described.

I claim as my invention:

1. A process for the production of an aromatic ester which comprises the steps of:
   (a) passing a feed stream comprising a $C_3$ and a $C_4$ olefin into an oligomerization zone operated at oligomerization-promoting conditions and effecting the production of an oligomerization zone effluent stream comprising $C_6$ to $C_{10}$ hydrocarbons including $C_7$ to $C_9$ acyclic olefinic hydrocarbons;
   (b) fractionating the oligomerization zone effluent stream into a light fraction comprising $C_6$ hydrocarbons, an intermediate fraction comprising $C_7$ to $C_9$ acyclic olefinic hydrocarbons and a heavy fraction comprising $C_{10}$ hydrocarbons;
   (c) contacting the intermediate fraction with a hydroformylation catalyst at hydroformylation conditions in admixture with carbon monoxide and hydrogen and effecting the production of a hydroformylation zone effluent stream comprising $C_8$ to $C_{10}$ acyclic aldehydes, $C_8$ to $C_{10}$ acyclic alcohols and at least 20 mole percent $C_7$ to $C_9$ acyclic olefinic hydrocarbons, with the hydroformylation conditions being effective to result in less than 60 mole percent of any dialkyl olefins and less than 90 mole percent of any trialkyl olefins present in the feed stream from being converted in said hydroformylation zone;
   (d) passing the entire hydroformylation zone effluent stream through a hydrogenation zone operated at aldehyde hydrogenation conditions and effecting the formation of a hydrogenation zone effluent stream;
   (e) fractionating the hydrogenation zone effluent stream into a light fraction comprising $C_7$ to $C_9$ acyclic olefinic hydrocarbons and a heavy fraction comprising $C_8$ to $C_{10}$ acyclic alcohols;
   (f) contacting the heavy fraction of the hydrogenation zone effluent stream with a monocyclic aromatic carboxylic acid or an aromatic anhydride in an esterification zone maintained at esterification-promoting conditions and effecting the production of an esterification zone effluent stream comprising an aromatic ester; and,
   (g) recovering the aromatic ester from the esterification zone effluent stream.

2. The process of claim 1 further characterized in that a high octane blending stock is simultaneously produced by admixing the light and heavy fractions of the oligomerization zone effluent stream and the light fraction of the hydrogenation zone effluent stream.

3. The process of claim 1 further characterized in that the monocyclic aromatic carboxylic acid is phthalic acid.

4. The process of claim 1 further characterized in that the aromatic anhydride is phthalic anhydride.

5. In a process for the production of aromatic esters useful as plasticizers wherein a feed stream comprising an acyclic olefinic hydrocarbon having between 6 and 9 carbon atoms per molecule is converted to an acyclic alcohol having from 8 to 10 carbon atoms per molecule through a series of steps which includes reacting the acyclic olefinic hydrocarbon with carbon monoxide and hydrogen in a hydroformylation zone, hydrogenating the effluent of the hydroformylation zone, and reacting the resultant acyclic alcohol with a monocyclic aromatic carboxylic acid or an aromatic anhydride in an esterification zone to produce an aromatic ester which is then recovered, the improvement which comprises producing the acyclic alcohol by passing a two carbon number range stream of the acyclic olefins through the hydroformylation zone at conditions being effective to result in less than 60 mole percent of any dialkyl olefins and less than 90 mole percent of any tri alkyl olefins present in the feed stream from being converted in said hydroformylation zone hydrogenating the effluent of the hydroformylation zone at aldehyde hydrogenation conditions to produce a hydrogenation zone effluent stream comprising acyclic alcohols and at least 20 mole percent acyclic olefinic hydrocarbons, separating the hydrogenation zone effluent stream into a light fraction comprising highly branched acyclic olefinic hydrocarbons and which is useful as a motor fuel blending stock and a heavy fraction comprising acyclic alcohols, and passing the heavy fraction into the esterification zone as the alcohol feed stream charged to the esterification zone.

6. The process of claim 5 further characterized in that the monocyclic aromatic carboxylic acid is phthalic acid.

* * * * *